US012042408B2

(12) United States Patent
Redkar et al.

(10) Patent No.: US 12,042,408 B2
(45) Date of Patent: Jul. 23, 2024

(54) PROSTHETIC LINER WITH SELECTIVE PRESSURE ADJUSTMENT

(71) Applicant: Arizona Board of Regents on behalf of Arizona State University, Scottsdale, AZ (US)

(72) Inventors: Sangram Redkar, Mesa, AZ (US); Zachery Shropshire, Phoenix, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 17/469,483

(22) Filed: Sep. 8, 2021

(65) Prior Publication Data

US 2022/0071783 A1 Mar. 10, 2022

Related U.S. Application Data

(60) Provisional application No. 63/076,019, filed on Sep. 9, 2020.

(51) Int. Cl.
| | |
|---|---|
| *A61F 2/78* | (2006.01) |
| *A61F 2/70* | (2006.01) |
| *A61F 2/74* | (2006.01) |
| *A61F 2/80* | (2006.01) |
| *A61F 2/50* | (2006.01) |
| *A61F 2/76* | (2006.01) |

(52) U.S. Cl.
CPC .............. *A61F 2/7843* (2013.01); *A61F 2/70* (2013.01); *A61F 2/748* (2021.08); *A61F 2/80* (2013.01); *A61F 2002/5007* (2013.01); *A61F 2002/5012* (2013.01); *A61F 2002/5032* (2013.01); *A61F 2002/704* (2013.01); *A61F 2002/7635* (2013.01)

(58) Field of Classification Search
CPC .......... A61F 2/7843; A61F 2/70; A61F 2/748; A61F 2/80; A61F 2002/5007; A61F 2002/5012; A61F 2002/5032; A61F 2002/704; A61F 2002/7635
See application file for complete search history.

(56) References Cited

U.S. PATENT DOCUMENTS

| 5,387,245 A * | 2/1995 | Fay ........................ A61F 2/7843 |
| | | 623/901 |
| 9,119,735 B2 * | 9/2015 | Accinni ..................... A61F 2/80 |
| 2003/0078674 A1 | 4/2003 | Phillips |
| 2009/0271000 A1 * | 10/2009 | Altobelli ................. A61F 5/012 |
| | | 29/527.3 |
| 2021/0128326 A1 * | 5/2021 | Tanriverdi ................ A61F 2/68 |

FOREIGN PATENT DOCUMENTS

WO WO-2019180431 A1 * 9/2019 ............... A61F 2/68

* cited by examiner

*Primary Examiner* — Bruce E Snow
(74) *Attorney, Agent, or Firm* — Riverside Law LLP

(57) ABSTRACT

A prosthetic liner for insertion within a socket of a prosthetic limb is provided. The prosthetic liner comprises a body having inflatable bladders and pressure sensors disposed thereon, an electronic circuit, one or more actuators, and a processor. The body receives a residual limb on an interior surface and contacts the socket on an exterior surface. The processor receives a digital pressure signal indicative of a detected pressure from each pressure sensor via the electronic circuit and selectively activates the actuators to adjust a pressure in one or more of the inflatable bladders based on the digital pressure signals and the region of the body corresponding to each digital pressure signal.

19 Claims, 4 Drawing Sheets

PROSTHETIC LINER WITH SELECTIVE PRESSURE ADJUSTMENT

CROSS-REFERENCE TO RELATED APPLICATIONS

This application claims the benefit of priority to U.S. Provisional Application No. 63/076,019 entitled "Prosthetic Liner with Selective Pressure Adjustment," filed Sep. 9, 2020, which is incorporated herein by reference in its entirety.

TECHNICAL FIELD

The present disclosure relates generally to an electronic prosthetic liner with pressure adjustment mechanisms. More particularly, the prosthetic liner may be disposed between a residual limb and a socket of a prosthetic limb and may include inflatable compartments to adjust a pressure at different regions of the liner to reduce pain, improve comfort, and prevent pistoning within the socket.

BACKGROUND

Prosthetic limbs are a common solution to improve quality of life for amputees. With an estimated 2 million leg amputees in the United States, several types of prosthetic limbs have been developed to recreate the structure and functionality of a human limb. Many prosthetic limbs include a socket for receiving the residual limb of the amputee and securing the prosthetic limb thereto.

However, various issues may arise with the fitting of a residual limb with a prosthetic socket. Sockets may be formed from rigid materials (e.g., carbon fiber) and thus may cause pain or discomfort to the residual limb, especially during extended use. Further, sockets are produced in standard, non-specialized sizes and often do not precisely fit the residual limbs of many amputees. In addition to pain and discomfort, ill-fitting sockets may lead to shifting of the residual limb within the socket during natural gait, often referred to as "pistoning." Over time, pistoning and excessive pressure or pain to the residual limb may lead to skin damage and/or harmful conditions, e.g., verrucous hyperplasia, intertriginous dermatitis, bacterial and fungal infections, chronic ulcers, and tumors.

Currently available solutions include liners or inserts designed to be placed over the residual limb to provide cushioning, support, and improved fit between the residual limb and the socket. While conventional liners and inserts do provide a degree of comfort, they do not provide significant impact protection. Liners and inserts also suffer from some of the same limitations as prosthetic limbs, such as being produced in standard, non-specialized sizes. Furthermore, liners and inserts typically provide uniform coverage and cannot be easily adjusted to provide greater support to areas of particular need.

Moreover, residual limbs may fluctuate in shape or size in various manners. While residual limbs may be somewhat bulbous or cylindrical after amputation, the residual limbs may become more conical in shape with age due to atrophy. Residual limbs may also fluctuate in volume throughout the course of days or weeks based on physical condition, weight gain or loss, physical state (e.g., perspiration), and the like. Accordingly, standard or non-adjustable means of providing comfort to the residual limb or fitting within a socket may be unsatisfactory as the specific requirements change frequently.

As such, it would be advantageous to have a prosthetic liner capable of customizing support for a particular user as well as redistributing pressure and adjusting for volume fluctuations in real time.

SUMMARY

This summary is provided to comply with 37 C.F.R. § 1.73. It is submitted with the understanding that it will not be used to interpret or limit the scope or meaning of the present disclosure.

A prosthetic liner for insertion within a socket of a prosthetic limb is provided. The prosthetic liner comprises a body having a radially inward surface configured to receive a residual limb, a radially outward surface configured to contact the socket, and a plurality of inflatable bladders disposed about the body; a plurality of pressure sensors disposed about the body in a spaced arrangement, each pressure sensor configured to detect a pressure at a region of the body; an electronic circuit configured to generate, for each pressure sensor, a digital pressure signal indicative of the detected pressure; one or more actuators configured to selectively inflate each of the plurality of inflatable bladders; a processor; and a non-transitory, computer-readable medium storing instructions that, when executed, cause the processor to: receive the digital pressure signal for each pressure sensor via the electronic circuit; and selectively activate the one or more actuators to adjust a pressure in one or more of the plurality of inflatable bladders based on the digital pressure signal for each pressure sensor and the region corresponding to each digital pressure signal.

According to some embodiments, each inflatable bladder comprises a valve configured to: in an open position, permit air to pass through the valve to change the pressure within the inflatable bladder; and in a closed position, maintain a pressure within the inflatable bladder.

According to some embodiments, the plurality of inflatable air bladders are disposed on the radially inward surface of the body.

According to some embodiments, the instructions, when executed, further cause the processor to selectively activate the one or more actuators to increase the pressure in one or more of the plurality of inflatable bladders in response to a detected pressure below a predetermined threshold.

According to some embodiments, the instructions, when executed, further cause the processor to selectively activate the one or more actuators to decrease the pressure in one or more of the plurality of inflatable bladders in response to a detected pressure above a predetermined threshold.

According to some embodiments, the body comprises a base portion configured to contact a stump of the residual limb at the radially inward surface and a tubular portion configured to contact a radial surface of the residual limb at the radially inward surface. According to additional embodiments, the base portion comprises a compressible material configured to reduce a contact pressure against the stump of the residual limb. According to further embodiments, the compressible material is selected from the group consisting of foam and silicone.

According to some embodiments, the prosthetic liner further comprises a wireless communication component configured to receive user input from a remote computing device and convey the user input to the processor, wherein the instructions, when executed, further cause the processor to selectively activate the one or more actuators to adjust the pressure in one or more of the plurality of inflatable bladders based on the user input.

According to some embodiments, the one or more actuators comprises one or more pumps. According to additional embodiments, the one or more pumps are configured to selectively pump air to each of the plurality of inflatable bladders.

According to some embodiments, the prosthetic liner further comprises a manifold including a plurality of fluid channels, wherein each fluid channel fluidly communicates with one of the plurality of inflatable bladders, wherein each fluid channel comprises a distribution valve configured to selectively permit fluid through the fluid channel. According to additional embodiments, the prosthetic liner further comprises an exterior valve configured to permit fluid from an exterior environment into the plurality of fluid channels of the manifold.

According to some embodiments, each of the plurality of inflatable bladders comprises a compressible tube disposed about the body. According to additional embodiments, each compressible tube is configured to selectively shift between a deflated, substantially planar configuration and an inflated, non-planar configuration. According to additional embodiments, each compressible tube is disposed in a substantially orthogonal orientation with respect to a longitudinal axis of the prosthetic liner. According to further embodiments, the plurality of inflatable bladders are axially spaced along the longitudinal axis of the prosthetic liner. According to additional embodiments, each compressible tube is disposed on the radially outward surface of the body.

According to some embodiments, each pressure sensor is in electrical communication with the processor through one or more interfacing components, wherein the one or more interfacing components comprise one or more printed electrical conductors disposed on the body.

According to some embodiments, the instructions, when executed, further cause the processor to: identify, for each region of the body, a pressure state of the region based on the digital pressure signal for each pressure sensor corresponding to the region, wherein the pressure state is selected from the group consisting of an insufficient pressure, an adequate pressure, and an excess pressure; and activate the one or more actuators to selectively inflate or deflate one or more of the plurality of inflatable bladders based on the pressure state of each region, thereby shifting each region of the body having an insufficient pressure to an adequate pressure and shifting each region of the body having an excess pressure to an adequate pressure.

A prosthetic liner for insertion within a socket of a prosthetic limb is also provided. The prosthetic liner comprises a body having: a radially inward surface configured to receive a residual limb, a radially outward surface configured to contact the socket, and a plurality of compressible tubes disposed about the body on the radially outward surface, wherein each compressible tube is configured to selectively shift between a deflated, substantially planar configuration and an inflated, non-planar configuration; a plurality of pressure sensors disposed about the body in a spaced arrangement, each pressure sensor configured to detect a pressure at a region of the body; an electronic circuit configured to generate, for each pressure sensor, a digital pressure signal indicative of the detected pressure; one or more actuators configured to selectively inflate each of the plurality of compressible tubes; a processor; and a non-transitory, computer-readable medium storing instructions that, when executed, cause the processor to: receive the digital pressure signal for each pressure sensor via the electronic circuit, and selectively activate the one or more actuators to adjust a pressure in one or more of the plurality of compressible tubes based on the digital pressure signal for each pressure sensor and the region corresponding to each digital pressure signal.

BRIEF DESCRIPTION OF THE DRAWINGS

The accompanying drawings, which are incorporated in and form a part of the specification, illustrate the embodiments of the invention and together with the written description serve to explain the principles, characteristics, and features of the invention. In the drawings.

DETAILED DESCRIPTION

Figure 1A:
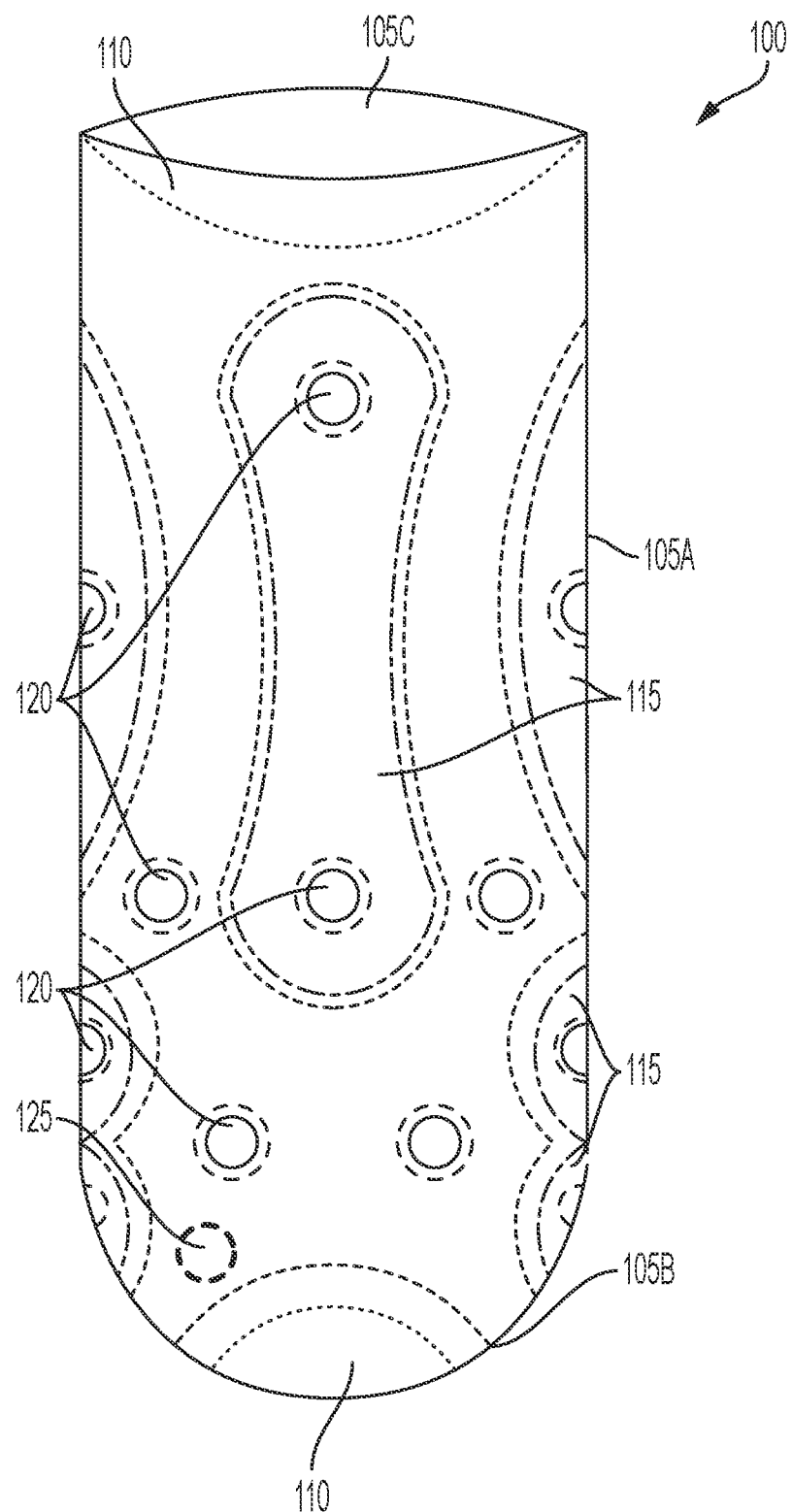
FIGS. 1A-1B depict partially transparent front and back views of an illustrative prosthetic liner in accordance with an embodiment.

This disclosure is not limited to the particular systems, devices and methods described, as these may vary. The terminology used in the description is for the purpose of describing the particular versions or embodiments only, and is not intended to limit the scope. Such aspects of the disclosure be embodied in many different forms; rather, these embodiments are provided so that this disclosure will be thorough and complete, and will fully convey its scope to those skilled in the art.

As used in this document, the singular forms "a," "an," and "the" include plural references unless the context clearly dictates otherwise. With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

As will be understood by one skilled in the art, for any and all purposes, such as in terms of providing a written description, all ranges disclosed herein are intended as encompassing each intervening value between the upper and lower limit of that range and any other stated or intervening value in that stated range. All ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art all language such as "up to," "at least," and the like include the number recited and refer to ranges that can be subsequently broken down into subranges as discussed above. Finally, as will be understood by one skilled in the art, a range includes each individual member. Thus, for example, a group having 1-3 cells refers to groups having 1, 2, or 3 cells as well as the range of values greater than or equal to 1 cell and less than or equal to 3 cells. Similarly, a group having 1-5 cells refers to groups having 1, 2, 3, 4, or 5 cells, as well as the range of values greater than or equal to 1 cell and less than or equal to 5 cells, and so forth.

In addition, even if a specific number is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, sample embodiments, or drawings, should be understood to contemplate the possibilities of including one of the terms, either of the terms, or both terms. For example, the phrase "A or B" will be understood to include the possibilities of "A" or "B" or "A and B."

In addition, where features of the disclosure are described in terms of Markush groups, those skilled in the art will recognize that the disclosure is also thereby described in terms of any individual member or subgroup of members of the Markush group.

All percentages, parts and ratios are based upon the total weight of the topical compositions and all measurements made are at about 25° C., unless otherwise specified.

The term "about," as used herein, refers to variations in a numerical quantity that can occur, for example, through measuring or handling procedures in the real world; through inadvertent error in these procedures; through differences in the manufacture, source, or purity of compositions or reagents; and the like. Typically, the term "about" as used herein means greater or lesser than the value or range of values stated by ¹⁄₁₀ of the stated values, e.g., ±10%. The term "about" also refers to variations that would be recognized by one skilled in the art as being equivalent so long as such variations do not encompass known values practiced by the prior art. Each value or range of values preceded by the term "about" is also intended to encompass the embodiment of the stated absolute value or range of values. Whether or not modified by the term "about," quantitative values recited in the present disclosure include equivalents to the recited values, e.g., variations in the numerical quantity of such values that can occur, but would be recognized to be equivalents by a person skilled in the art. Where the context of the disclosure indicates otherwise, or is inconsistent with such an interpretation, the above-stated interpretation may be modified as would be readily apparent to a person skilled in the art. For example, in a list of numerical values such as "about 49, about 50, about 55, "about 50" means a range extending to less than half the interval(s) between the preceding and subsequent values, e.g., more than 49.5 to less than 52.5. Furthermore, the phrases "less than about" a value or "greater than about" a value should be understood in view of the definition of the term "about" provided herein.

It will be understood by those within the art that, in general, terms used herein are generally intended as "open" terms (for example, the term "including" should be interpreted as "including but not limited to," the term "having" should be interpreted as "having at least," the term "includes" should be interpreted as "includes but is not limited to," et cetera). Further, the transitional term "comprising," which is synonymous with "including," "containing," or "characterized by," is inclusive or open-ended and does not exclude additional, unrecited elements or method steps. While various compositions, methods, and devices are described in terms of "comprising" various components or steps (interpreted as meaning "including, but not limited to"), the compositions, methods, and devices can also "consist essentially of" or "consist of the various components and steps, and such terminology should be interpreted as defining essentially closed-member groups. By contrast, the transitional phrase" consisting of excludes any element, step, or ingredient not specified in the claim. The transitional phrase "consisting essentially of" limits the scope of a claim to the specified materials or steps "and those that do not materially affect the basic and novel characteristic(s)" of the claimed invention.

The term "real-time" is used to refer to calculations or operations performed on-the-fly as events occur or input is received by the operable system. However, the use of the term "real-time" is not intended to preclude operations that cause some latency between input and response, so long as the latency is an unintended consequence induced by the performance characteristics of the machine.

By hereby reserving the right to proviso out or exclude any individual members of any such group, including any sub-ranges or combinations of sub-ranges within the group, that can be claimed according to a range or in any similar manner, less than the full measure of this disclosure can be claimed for any reason. Further, by hereby reserving the right to proviso out or exclude any individual substituents, structures, or groups thereof, or any members of a claimed group, less than the full measure of this disclosure can be claimed for any reason. Throughout this disclosure, various patents, patent applications and publications are referenced. The disclosures of these patents, patent applications and publications are incorporated into this disclosure by reference in their entireties in order to more fully describe the state of the art as known to those skilled therein as of the date of this disclosure. This disclosure will govern in the instance that there is any inconsistency between the patents, patent applications and publications cited and this disclosure.

Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention.

As discussed herein, it would be advantageous to have a prosthetic liner with variable volume to adjust the pressure within the prosthetic socket. As generally described herein, residual limbs may have a fluctuating volume which may lead to discomfort, tissue damage and/or infection of the residual limb, and instability of the prosthetic limb (i.e., pistoning of the residual limb within the prosthetic socket). Ideally, a prosthetic liner could be configured to compensate for fluctuating volume of the residual limb and individually adjust pressure at different locations of the prosthetic liner based on pressure measurements.

Figure 1B:
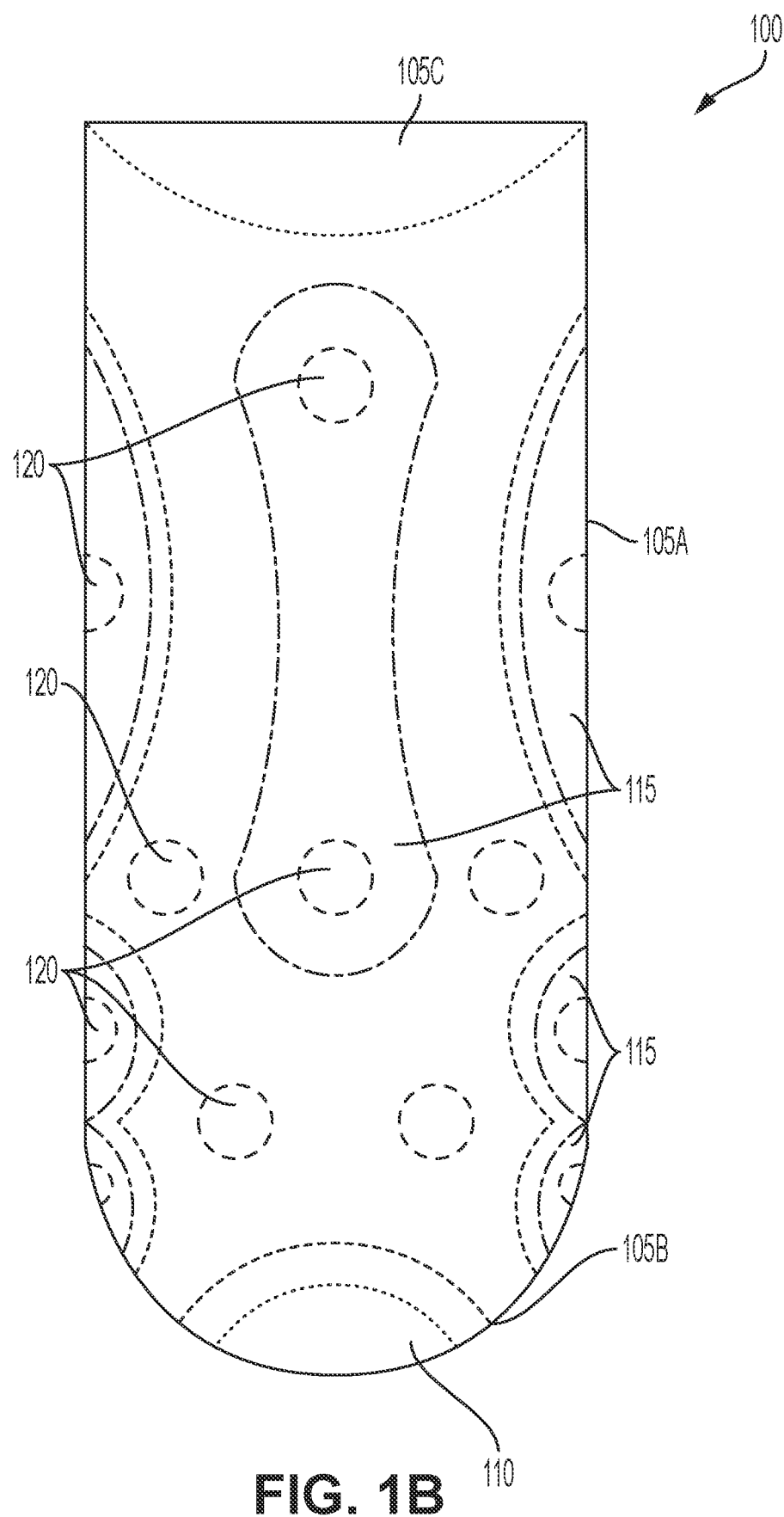
Figure 2:
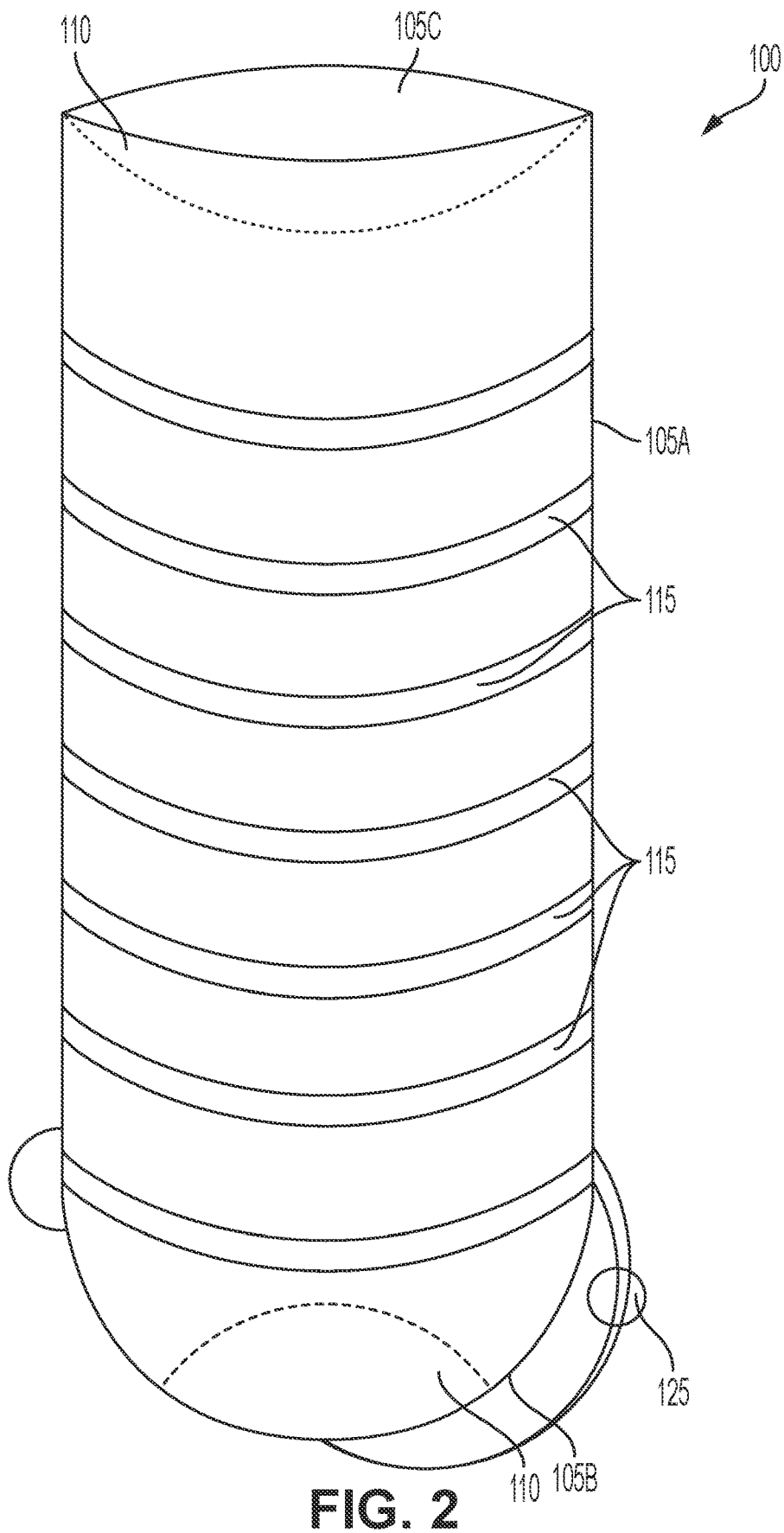
FIG. 2 depicts an illustrative prosthetic liner in accordance with an alternate embodiment.

FIGS. 1A-1B depict partially transparent front and back views of an illustrative prosthetic liner in accordance with an embodiment. FIG. 2 depicts an illustrative prosthetic liner in accordance with an alternate embodiment. Similar features within FIGS. 1-2 are identified with common reference numbers.

As shown in FIGS. 1-2, the prosthetic liner 100 comprises a liner body 105, a plurality of inflatable bladders 115, one or more sensing elements 120, and a pressure control system (not shown).

The liner body 105 may comprise a tubular portion 105A, base portion 105B at one end of the tubular portion 105A, and an open end 105C opposing the base portion 105B. Furthermore, the liner body 105 may comprise an interior surface facing towards a longitudinal axis of the liner body 105 and an exterior surface facing away from the longitudinal axis. In some embodiments, the open end 105C may be configured to receive a residual limb of a user (i.e., an amputee) therethrough, and the interior surface may be configured to contact the residual limb. In some embodiments, the exterior surface may be configured to be received within a socket of a prosthetic limb.

The liner body 105 may be formed from a variety of materials. In some embodiments, the liner body 105 may be formed from fabrics, olefins, nylon, acrylic, polyester, spandex, latex (e.g., Talalay latex and/or Dunlop latex), and/or elastomers. In some embodiments, the liner body 105 may have sufficient elasticity to grip and/or conform to the residual limb. Furthermore, the liner body 105 may include one or more layers of material configured to provide additional comfort and/or cushioning to the residual limb. For example, the liner body may include one or more cushioning layers 110 formed from gel, foam (e.g., memory foam or viscoelastic foam), and/or silicone to provide additional comfort. As shown in FIGS. 1-2, the one or more cushioning layers 110 may be provided at the base portion 105B and/or near the open end 105C. However, cushioning layers 110 may be provided in additional regions of the liner body as would be apparent to a person having an ordinary level of skill in the art. The layers of materials may be secured to one another by conventional manufacturing techniques. As shown in FIGS. 1-2, the cushioning layers 110 may be sealed or encased by the material forming the remainder of the liner body 105 and/or additional sealing materials. Additional layers or materials are contemplated herein for additional comfort and support.

In some embodiments, the liner body 105 may include gripping features such as bumps, ridges, grooves, protuberances, a textured surface, or other features to facilitate gripping. For example, the interior surface may include gripping features configured to grip a portion of the residual limb. In another example, the exterior surface may include gripping features configured to grip a portion of the socket of the prosthetic limb.

The plurality of inflatable bladders 115 may be configured to be expanded by receiving a fluid therein (e.g., air) and contracted by expelling a fluid therefrom. Accordingly, the volume of the inflatable bladders 115 may be adjusted to occupy additional volume within the socket of the prosthetic limb and/or to relieve pressure on a portion of the residual limb within the socket. In some embodiments, the inflatable bladders are configured to sit flat against the liner body 105 in a contracted position to provide greater comfort and minimize bunching or bulging of the prosthetic liner 100.

The plurality of inflatable bladders 115 may take a variety of forms. For example, FIGS. 1A-1B depict inflatable bladders 115 as expandable pockets that are sewn into the interior surface of the liner body 105 in a vertical orientation (i.e., elongated in a direction substantially parallel to the longitudinal axis of the liner body 105). In another example, FIG. 2 depicts inflatable bladders 115 as expandable tubular elements secured to the exterior surface of the liner body 105 in a horizontal orientation (i.e., elongated in a direction substantially orthogonal to the longitudinal axis of the liner body 105). However, alternate configurations of the inflatable bladders 115 are contemplated herein.

In some embodiments, the inflatable bladders 115 are disposed on the interior surface of the liner body 105 (e.g., as shown in FIGS. 1A-1B). In some embodiments, the inflatable bladders 115 may be disposed on the exterior surface of the liner body 105 (e.g., as shown in FIG. 2). In some embodiments, the inflatable bladders are formed as pockets and/or tubular elements. However, the inflatable bladders 115 may be formed in any shape as would be apparent to a person having an ordinary level of skill in the art. In some embodiments, the inflatable bladders 115 may be vertically oriented or horizontally oriented. In still other embodiments, the inflatable bladders 115 may be oriented at additional angles with respect to the longitudinal axis of the liner body 105 and/or combinations of angles as described. In some embodiments, it may be advantageous to form the inflatable bladders 115 from a resilient material. However, any of the materials described with respect to the liner body 105 may be used to form the inflatable bladders 115. In some embodiments, the inflatable bladders 115 are sewn onto the liner body 105 by one or more seams (e.g., as depicted in FIGS. 1A-1B as broken lines). In some embodiments, the inflatable bladders 115 are secured by adhesives, heat curing, chemical bonding, fasteners, and/or additional means as would be apparent to a person having an ordinary level of skill in the art. In some embodiments, the inflatable bladders 115 are integrally formed with the liner body 105, e.g., by a manufacturing process that produces the liner body 105 with the inflatable bladders 105 thereon as a unitary body.

The inflatable bladders 115 may also be arranged in a variety of manners. For example, where an inflatable bladder 115 is horizontally oriented, each inflatable bladder 115 may extend about the entire circumference of the liner body 105 (e.g., as shown in FIG. 2). In another example, where an inflatable bladder 115 is vertically oriented, each inflatable bladder 115 may extend an entire length of the liner body 105. However, the inflatable bladders 115 may extend a length less than the entire circumference and/or length of the liner body 105 (e.g., as shown in FIGS. 1A-1B). In some embodiments, the inflatable bladders 115 are arranged in rows or columns. For example, as shown in FIGS. 1A-1B, the inflatable bladders 115 may be arranged in multiple rows and/or columns. In some embodiments, the rows or columns may be staggered. Each inflatable bladder 115 may be configured to adjust a pressure on the liner body 105 at a zone or region where the inflatable bladder 115 is disposed. For example, where a patient experiences discomfort or pain at a portion of the residual limb while wearing the prosthetic liner and prosthetic limb, one or more inflatable bladders 115 in a corresponding region of the liner body 105 may be inflated to reduce a pressure against the residual limb. In some embodiments, the inflatable bladders 115 may be located in specific regions typically associated with pain, discomfort, tissue damage, and other issues associated with prosthetic limbs. In some embodiments, the inflatable bladders 115 may be arranged to provide coverage of all or substantially all of the surface of the liner body 105 such that pressure may be adjusted in any region of the liner body 105. Additional or alternate arrangements of the inflatable bladders 115 may be possible as would be apparent to a person having an ordinary level of skill in the art.

The one or more sensing elements 120 may be disposed on the liner body 105 to form a sensor array. The one or more sensing elements 120 (e.g., pressure sensors) may be integrally formed with the liner body 105 or affixed thereto by stitching (as depicted in FIGS. 1A-1B as broken lines), embedding, adhering, heat-sealing, or any other method known to one having ordinary skill in the art. In some embodiments, the sensor array comprises one or more sensing elements 120 such as pressure sensitive variable capacitors, pressure sensitive variable resistors, pressure transducers, force transducers, or other elements capable of sensing a pressure or force, which may be individually disposed on the liner body 105. In some embodiments, the sensor array comprises a piezoresistive array. For example, the sensor array may comprise two stacked thin polymer sheets having electrical conductors printed thereon and piezoresistive material applied in multiple intersecting layers to form individual sensing elements 120. As pressure is applied to the sensor array, the piezoresistive material of a given sensing element 120 may compress, thus changing the resistance and registering an electrical signal indicative of a pressure measurement. The sensor array may be implemented in additional ways as would be apparent to a person having an ordinary level of skill in the art. The prosthetic liner 100 may also include circuitry that converts a pressure detected by the sensing elements into a digital pressure signal.

In some embodiments, the sensing elements 120 may be disposed on the interior surface of the liner body 105 to directly sense a pressure against the residual limb. However, the sensing elements 120 may be disposed on the exterior surface of the liner body 105 and/or embedded within the liner body 105. In some embodiments, the sensor array may be directly incorporated as an integral feature of the liner body 105. For example, the liner body 105 may comprise a smart textile material, such as a piezoelectric fabric produced by BODITRAK or other smart textiles having passive or active sensing elements incorporated therein.

The sensing elements 120 of the sensor array may be arranged in a variety of manners. As shown in FIG. 1A, one or more pressure sensors 120 may be superimposed on the inflatable bladders 115 in order to sense a pressure directly over the inflatable bladders 115. Additionally or alternatively, one or more pressure sensors 120 may be disposed adjacent to inflatable bladders 115. In some embodiments, the sensing elements 120 are arranged in a grid pattern of intersecting rows and columns. In some embodiments, the sensing elements 120 may be arranged in a staggered pattern in the same manner as the inflatable bladders 115. For example, the sensing elements may be arranged in a diamond grid pattern. In some embodiments, the sensing elements 120 may be located in specific regions typically associated with pain, discomfort, tissue damage, and other issues associated with prosthetic limbs. In some embodiments, the sensing elements 120 may be arranged to provide coverage of all or substantially all of the surface of the liner body 105 such that pressure may be measured in any region of the liner body 105. Additional or alternate arrangements of the sensing elements 120 may be possible as would be apparent to a person having an ordinary level of skill in the art. Furthermore, a variety of densities of sensing elements 120 may be provided to form the sensor array. It is generally understood that a greater density results in greater resolution.

Further, the prosthetic liner 100 may comprise one or more interfacing components (not shown) for transmitting signals from the sensing elements 120 of the sensor array. For example, the prosthetic liner 100 may include interfacing components to place each sensing element 120 in electrical communication with a processor as described further herein to transmit signals from the sensor array. In some embodiments, the interfacing components comprise wires or printed electrical conductors in the liner body 105. However, any manner of electrical communication known to one having ordinary skill in the art may be implemented.

The pressure control system may comprise one or more actuators and a processor configured to control the one or more actuators to selectively inflate and/or deflate the inflatable bladders 115. In some embodiments, the one or more actuators may comprise electric actuators and/or pneumatic actuators. In some embodiments, the one or more actuators may include a pump and/or a motor to transport a fluid in and out of the inflatable bladders 115 in a controlled manner. For example, the actuators may transport air from an external environment (i.e., atmospheric air) into the inflatable bladders 115 and expel air from the inflatable bladders 115 into the external environment. However, in some embodiments, air or another fluid may be stored in a reservoir and transported between the inflatable bladders 115 and the reservoir to adjust the pressure in the inflatable bladders 115.

In some embodiments, the pressure control system may include a manifold configured to selectively direct fluid to and from each of the inflatable bladders 115. For example, the manifold may fluidly communicate with each of the inflatable bladders 115 through individual channels (e.g., channels extending through the liner body 105). In some embodiments, each channel may include a distribution valve configured to control fluid passage through the channel. For example, each distribution valve may be configured to permit fluid passage through the corresponding channel in an open position and prohibit fluid passage through the channel in the closed position. While each inflatable bladder 115 may include a valve, in some embodiments, inflatable bladders 115 within a zone or region may have a single valve and may thus be inflated and/or deflated together. In additional embodiments, the inflatable bladders 115 may be connected in series by channels extending therebetween with distribution valves arranged between pairs of inflatable bladders 115 or pairs of zones of inflatable bladders 115.

As shown in FIGS. 1-2, the pressure control system may include an exterior port 125 including a valve (e.g., a two-way valve) configured to draw air into the manifold from the external environment and release air from the manifold to the external environment. However, in some embodiments, the pressure control system may utilize multiple one-way ports to perform the same function. For example, the pressure control system may include an intake port including a valve (e.g., a one-way valve or a check valve) configured to draw air into the pressure control system (i.e., the manifold and/or channels) for distribution to the inflatable bladders 115 and an exhaust port including a valve (e.g., a one-way valve or a check valve) configured to expel air from the pressure control system to the external environment.

Each of the valves described herein may be in electrical communication with the processor and thereby controlled by the processor to selectively open and close. The valves described herein may be solenoid valves, ball valves, gate valves, check valves, butterfly valves, globe valves, needle valves, switching valves, and/or additional types of valves as would be apparent to a person having an ordinary level of skill in the art.

In some embodiments, the prosthetic liner 100 may include a power source in electrical communication with the processor, the sensing elements 120, the actuators, and the valves. In some embodiments, the power source may include a battery. An electrical connection may be used to connect the power source to various components. For example, the electrical connection may comprise a wired connection. In some embodiments, the power source is integrated with processor and/or additional control circuitry.

In some embodiments, the processor may be configured to receive pressure signals from each of the sensing elements 120 indicative of a measured pressure and instruct inflation and/or deflation based on the measured pressures in order to reduce pain, increase comfort, account for volume fluctuations, and/or prevent pistoning. During inflation, the processor may instruct the distribution valves to selectively open and close the channels to the inflatable bladders 115 and may instruct the actuators to transport fluid through the exterior port 125, through the channels and into the inflatable bladders 115. During deflation, the processor may instruct the distribution valves to selectively open and close the channels to the inflatable bladders 115 and may instruct the actuators to transport fluid out of the inflatable bladders 115, through the channels and out of the exterior port 125 (i.e., active deflation). However, in other embodiments, the processor may instruct the distribution valves to selectively open and close the channels to the inflatable bladders 115 and instruct opening of the exterior port 125, thereby allowing escape of air and deflation of the inflatable bladders 115 (i.e., passive deflation).

In some embodiments, the processor may instruct inflation and deflation based on predetermined pressure values or ranges of values. For example, the processor may compare measured pressures from each sensing element 120 to expected or standard pressure values corresponding to the location of each sensing element 120. In some embodiments, the predetermined pressure values may be based on clinical data, user data from a plurality of historical users, and/or user data specific to an individual (e.g., the current user). The predetermined pressure value may be different for each sensing element 120. In some embodiments, the predetermined pressure values may be based on user input. For example, a user may provide input to adjust pressure in each zone or region based on personal comfort or preference. Thereafter, the processor may control inflation and deflation of the inflatable bladders 115 to maintain the pressure at each sensing element at the predetermined pressure value or within the predetermined pressure range.

In some embodiments, the processor may instruct deflation of an inflatable bladder 115 in response to a measured pressure greater than the corresponding predetermined pressure for the sensing element 120. Accordingly, pressure may be relieved in a region of the socket in order to provide greater comfort and/or reduce pain at the residual limb of the user. In some embodiments, the processor may instruct inflation of an inflatable bladder 115 in response to a measured pressure less than the corresponding predetermined pressure for the sensing element 120. Accordingly, pressure may be increased in a region of the socket in order to reduce movement of the residual limb within the socket and prevent pistoning within the socket. The processor may receive measured pressures from the sensing elements 120 in real time and may thus adjust the pressure in the inflatable bladders until adequate measured pressures are obtained. However, the pressure may be adjusted in response to measured pressures in a variety of ways. For example, in response to exceeding pressure in a region, the processor may further increase pressure in the region and/or decrease pressure at an opposing region of the prosthetic liner 100, thereby shifting the residual limb away from the surface of the socket in the region of exceeding pressure and providing additional cushioning via inflation of the inflatable bladders 115. Despite adequate pressure in a region, a user may wish to increase pressure to provide additional cushioning between the residual limb and a surface of the socket. Additional types of adjustments are contemplated herein as would be apparent to a person having an ordinary level of skill in the art.

In some embodiments, pressures for a plurality of inflatable bladders 115 may be concurrently adjusted in order to adjust a measured pressure at a single sensing element 120. For example, the processor may selectively adjust pressures in inflatable bladders 115 adjacent to the sensing element 120 and/or in the zone or region of the sensing element 120 to adjust the measured pressure at the sensing element 120. However, as described, the processor may selectively adjust pressures in inflatable bladders 115 in additional regions (e.g., an opposing region to the sensing element 120) to adjust the measured pressure.

The devices, systems, and methods as described herein are not intended to be limited in terms of the particular embodiments described, which are intended only as illustrations of various features. Many modifications and variations to the devices, systems, and methods can be made without departing from their spirit and scope, as will be apparent to those skilled in the art.

In some embodiments, the prosthetic liner 100 may include a manual air pump configured to inflate and/or deflate the inflatable bladders 115 and/or one or more manual release mechanisms configured to deflate the inflatable bladders 115. Accordingly, a user may be able to adjust or fine tune the pressure in each of the inflatable bladders 115 based on comfort and/or preference.

In some embodiments, the prosthetic liner may include a wireless transmission component configured to exchange information with a remote computing device, e.g., a computer, a mobile phone, a tablet, and/or the like. For example, the wireless transmission component may use a wireless technology such as, without limitation, Wi-Fi, Bluetooth, Near Field Communication (NFC), or ZigBee. The wireless transmission component may transmit information between the remote computing device and the processor. In some embodiments, user input may be received via a user interface of the remote computing device (e.g., a dedicated software application) and transmitted to the processor to be used in controlling the prosthetic liner 100. In some embodiments, a user may provide user input to manually adjust pressure in one or more regions of the prosthetic liner 100 in real time. In some embodiments, the user may provide user input to set or modify standard settings of the pressure control. For example, the user may indicate a general level of desired pressure and/or set a desired pressure at one or more regions of the prosthetic liner 100. Accordingly, the processor may conform the instructions (e.g., predetermined pressure values) to the user input. In some embodiments, the user may perform an initial calibration to set the pressure conditions of the prosthetic liner 100 as desired based on comfort and/or preference, and the processor may use the settings from the initial calibration to conform the instructions thereto. In some embodiments, the user input and/or calibration settings may be stored and used as baseline settings in future instances.

In some embodiments, the prosthetic liner may be designed and configured for use with a prosthetic limb of a specific make and/or model. Therefore, while various components may be disposed on the prosthetic liner 100 as described herein, it should be understood that any number of components may be relocated to a portion of the prosthetic limb. For example, the processor, the power source, the actuators, the sensing elements 120, and/or additional components may be located on the prosthetic limb (e.g., within or adjacent to the socket). The prosthetic liner may interface with the prosthetic limb via an interface component (e.g., a wired adapter) in order to provide electrical and/or fluid communication between components as described herein. Accordingly, the prosthetic liner 100 may contain fewer components in order to simplify manufacturing and reduce the associated costs.

In some embodiments, the prosthetic liner 100 is designed for use on a residual leg, e.g., a residual leg of an above-knee amputee. However, the prosthetic liner 100 may be adapted for use on a residual leg of a below-knee amputee and/or a residual arm with minor modifications as would be apparent to a person having an ordinary level of skill in the art.

In some embodiments, the prosthetic liner 100 may be designed as a re-usable component and may be configured to be washed and/or sterilized. In some embodiments, the prosthetic liner 100 may be designed as a disposable component and may be configured for one-time use.

Figure 3:
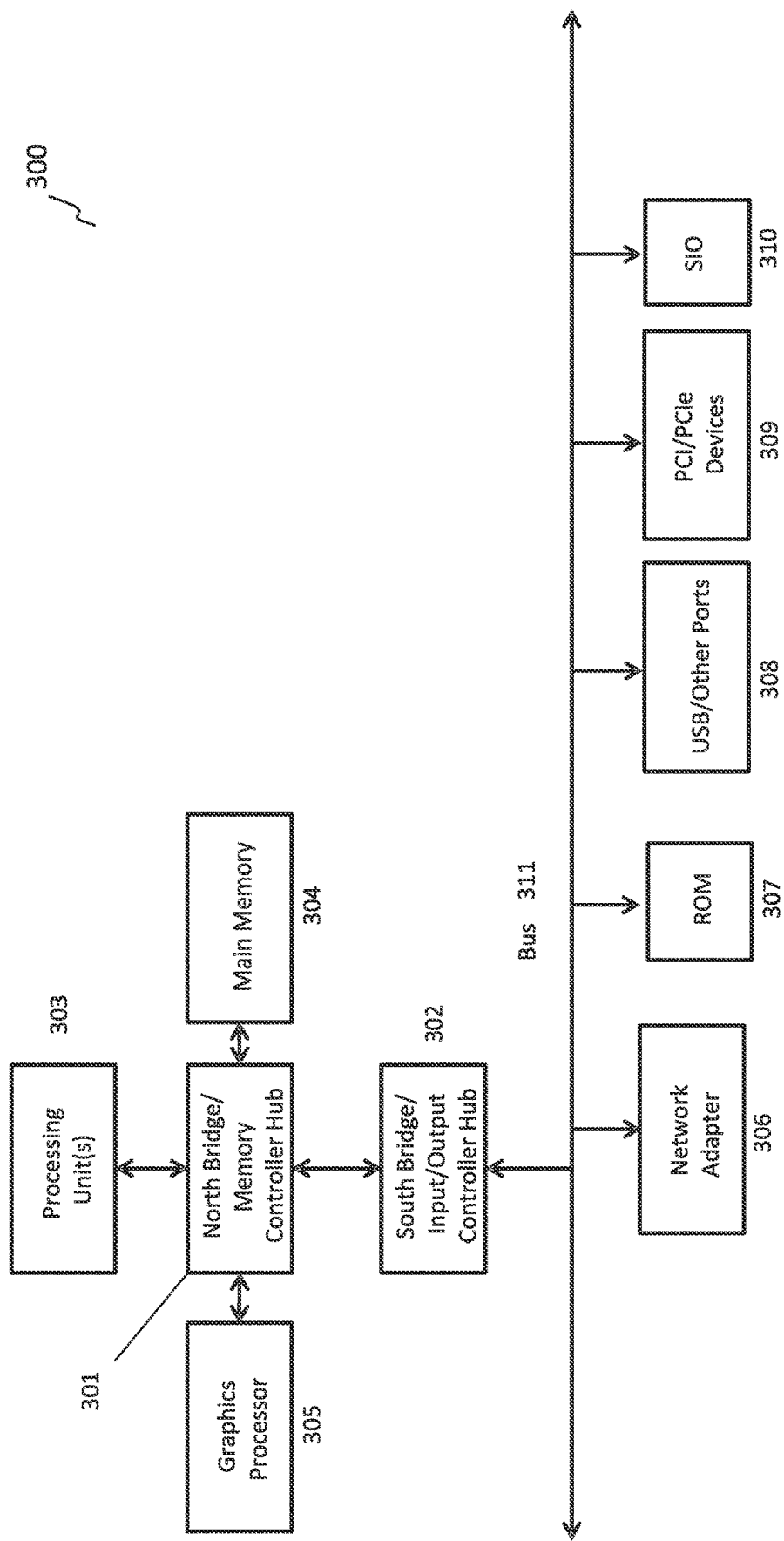
FIG. 3 depicts a block diagram of an illustrative data processing system in which aspects of the illustrative embodiments are implemented.

FIG. 3 illustrates a block diagram of an illustrative data processing system 300 in which aspects of the illustrative embodiments are implemented. The data processing system 300 is an example of a computer, such as a server or client, in which computer usable code or instructions implementing the process for illustrative embodiments of the present invention are located. In some embodiments, the data processing system 300 may comprise a computing device operably connected to a prosthetic liner 100 as described above (e.g., as part of the prosthetic liner 100 or as a remote device in communication therewith). The data processing system 300 can be configured to, for example, transmit and receive information related to a user.

In the depicted example, data processing system 300 can employ a hub architecture including a north bridge and memory controller hub (NB/MCH) 301 and south bridge and input/output (I/O) controller hub (SB/ICH) 302. Processing unit 303, main memory 304, and graphics processor 305 can be connected to the NB/MCH 301. Graphics processor 305 can be connected to the NB/MCH 301 through, for example, an accelerated graphics port (AGP).

In the depicted example, a network adapter 306 connects to the SB/ICH 302. A read only memory (ROM) 307, universal serial bus (USB) ports and other communication ports 308, and PCI/PCIe devices 309 may connect to the SB/ICH 302 through bus system 311. PCI/PCIe devices 309 may include Ethernet adapters, add-in cards, and PC cards for notebook computers. ROM 307 may be, for example, a flash basic input/output system (BIOS). A super I/O (SIO) device 310 can be connected to the SB/ICH 302.

An operating system can run on the processing unit 303. The operating system can coordinate and provide control of various components within the data processing system 300. As a client, the operating system can be a commercially available operating system. An object-oriented programming system, such as the Java™ programming system, may run in conjunction with the operating system and provide calls to the operating system from the object-oriented programs or applications executing on the data processing system 300. As a server, the data processing system 300 can be an IBM® eServer™ System® running the Advanced Interactive Executive operating system or the Linux operating system. The data processing system 300 can be a symmetric multiprocessor (SMP) system that can include a plurality of processors in the processing unit 303. Alternatively, a single processor system may be employed.

Instructions for the operating system, the object-oriented programming system, and applications or programs are located on storage devices, and are loaded into the main memory 304 for execution by the processing unit 303. The processes for embodiments described herein can be performed by the processing unit 303 using computer usable program code, which can be located in a memory such as, for example, main memory 304, ROM 307, or in one or more peripheral devices.

A bus system 311 can be comprised of one or more busses. The bus system 311 can be implemented using any type of communication fabric or architecture that can provide for a transfer of data between different components or devices attached to the fabric or architecture. A communication unit such as the network adapter 306 can include one or more devices that can be used to transmit and receive data.

Those of ordinary skill in the art will appreciate that the hardware depicted in FIG. 3 may vary depending on the implementation. Other internal hardware or peripheral devices, such as flash memory, equivalent non-volatile memory, or optical disk drives may be used in addition to or in place of the hardware depicted. Moreover, the data processing system 300 can take the form of any of a number of different data processing systems, including but not limited to, client computing devices, server computing devices, tablet computers, laptop computers, telephone or other communication devices, personal digital assistants, and the like. Essentially, data processing system 300 can be any known or later developed data processing system without architectural limitation.

In the above detailed description, reference is made to the accompanying drawings, which form a part hereof. In the drawings, similar symbols typically identify similar components, unless context dictates otherwise. The illustrative embodiments described in the present disclosure are not meant to be limiting. Other embodiments may be used, and other changes may be made, without departing from the spirit or scope of the subject matter presented herein. It will be readily understood that various features of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various features. Instead, this application is intended to cover any variations, uses, or adaptations of the present teachings and use its general principles. Further, this application is intended to cover such departures from the present disclosure as come within known or customary practice in the art to which these teachings pertain. Many modifications and variations can be made to the particular embodiments described without departing from the spirit and scope of the present disclosure, as will be apparent to those skilled in the art. Functionally equivalent methods and apparatuses within the scope of the disclosure, in addition to those enumerated herein, will be apparent to those skilled in the art from the foregoing descriptions. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A prosthetic liner for insertion within a socket of a prosthetic limb, the prosthetic liner comprising:
a body having a radially inward surface configured to receive a residual limb, a radially outward surface configured to contact the socket, and a plurality of inflatable air bladders disposed about the body;
a plurality of pressure sensors disposed on the radially inward surface of the body in a spaced arrangement, each pressure sensor configured to directly detect a pressure against the residual limb at a region of the body;
an electronic circuit configured to generate, for each pressure sensor, a digital pressure signal indicative of the detected pressure;
one or more air pumps configured to selectively inflate each of the plurality of inflatable air bladders with air;
a processor; and
a non-transitory, computer-readable medium storing instructions that, when executed, cause the processor to:
receive the digital pressure signal for each pressure sensor via the electronic circuit, and
selectively activate the one or more air pumps to adjust a pressure in one or more of the plurality of inflatable air bladders based on the digital pressure signal for each pressure sensor and the region corresponding to each digital pressure signal.

2. The prosthetic liner of claim 1, wherein each inflatable air bladder comprises a valve configured to:
in an open position, permit air to pass through the valve to change the pressure within the inflatable bladder; and
in a closed position, maintain a pressure within the inflatable air bladder.

3. The prosthetic liner of claim 1, wherein the plurality of inflatable air bladders are disposed on the radially inward surface of the body.

4. The prosthetic liner of claim 1, wherein the instructions, when executed, further cause the processor to selectively activate the one or more air pumps to increase the pressure in one or more of the plurality of inflatable air bladders in response to a detected pressure below a predetermined threshold.

5. The prosthetic liner of claim 1, wherein the instructions, when executed, further cause the processor to selectively activate the one or more air pumps to decrease the pressure in one or more of the plurality of inflatable air bladders in response to a detected pressure above a predetermined threshold.

6. The prosthetic liner of claim 1, wherein the body comprises a base portion configured to contact a stump of the residual limb at the radially inward surface and a tubular portion configured to contact a radial surface of the residual limb at the radially inward surface.

7. The prosthetic liner of claim 6, wherein the base portion comprises a compressible material configured to reduce a contact pressure against the stump of the residual limb.

8. The prosthetic liner of claim 7, wherein the compressible material is selected from the group consisting of foam and silicone.

9. The prosthetic liner of claim 1, further comprising a wireless communication component configured to receive user input from a remote computing device and convey the user input to the processor,
wherein the instructions, when executed, further cause the processor to selectively activate the one or more air pumps to adjust the pressure in one or more of the plurality of inflatable air bladders based on the user input.

10. The prosthetic liner of claim 1, further comprising a manifold including a plurality of fluid channels, wherein each fluid channel fluidly communicates with one of the plurality of inflatable air bladders,
wherein each fluid channel comprises a distribution valve configured to selectively permit air through the fluid channel.

11. The prosthetic liner of claim 10, further comprising an exterior valve configured to permit fluid from an exterior environment into the plurality of fluid channels of the manifold.

12. The prosthetic liner of claim 1, wherein each of the plurality of inflatable air bladders comprises a compressible tube disposed about the body.

13. The prosthetic liner of claim 12, wherein each compressible tube is configured to selectively shift between a deflated, substantially planar configuration and an inflated, non-planar configuration.

14. The prosthetic liner of claim 12, wherein each compressible tube is disposed in a substantially orthogonal orientation with respect to a longitudinal axis of the prosthetic liner.

15. The prosthetic liner of claim 14, wherein the plurality of inflatable air bladders are axially spaced along the longitudinal axis of the prosthetic liner.

16. The prosthetic liner of claim 12, wherein each compressible tube is disposed on the radially outward surface of the body.

17. The prosthetic liner of claim 1, wherein each pressure sensor is in electrical communication with the processor through one or more interfacing components, wherein the one or more interfacing components comprise one or more printed electrical conductors disposed on the body.

18. The prosthetic liner of claim 1, wherein the instructions, when executed, further cause the processor to:
identify, for each region of the body, a pressure state of the region based on the digital pressure signal for each pressure sensor corresponding to the region, wherein the pressure state is selected from the group consisting of an insufficient pressure, an adequate pressure, and an excess pressure; and
activate the one or more air pumps to selectively inflate or deflate one or more of the plurality of inflatable air bladders based on the pressure state of each region, thereby shifting each region of the body having an insufficient pressure to an adequate pressure and shifting each region of the body having an excess pressure to an adequate pressure.

19. A prosthetic liner for insertion within a socket of a prosthetic limb, the prosthetic liner comprising:
a body having:
a radially inward surface configured to receive a residual limb,
a radially outward surface configured to contact the socket, and
a plurality of compressible tubes disposed about the body on the radially outward surface, wherein each compressible tube is configured to selectively shift between a deflated, substantially planar configuration and an inflated, non-planar configuration;
a plurality of pressure sensors disposed on the radially inward surface of the body in a spaced arrangement, each pressure sensor configured to directly detect a pressure against the residual limb at a region of the body;

an electronic circuit configured to generate, for each pressure sensor, a digital pressure signal indicative of the detected pressure;

one or more air pumps configured to selectively inflate each of the plurality of compressible tubes with air;

a processor; and a non-transitory, computer-readable medium storing instructions that, when executed, cause the processor to:
  receive the digital pressure signal for each pressure sensor via the electronic circuit, and
  selectively activate the one or more air pumps to adjust a pressure in one or more of the plurality of compressible tubes based on the digital pressure signal for each pressure sensor and the region corresponding to each digital pressure signal.

* * * * *